US012193381B2

(12) United States Patent
Berg et al.

(10) Patent No.: US 12,193,381 B2
(45) Date of Patent: *Jan. 14, 2025

(54) CELERY MORPHOLOGY

(71) Applicant: RIJK ZWAAN ZAADTEELT EN ZAADHANDEL B.V., De Lier (NL)

(72) Inventors: Jurjen Johannes Berg, De Lier (NL); Reinier Hendrik Marie Deneer, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 399 days.

This patent is subject to a terminal disclaimer.

(21) Appl. No.: 18/054,639

(22) Filed: Nov. 11, 2022

(65) Prior Publication Data
US 2023/0073853 A1 Mar. 9, 2023

Related U.S. Application Data

(63) Continuation of application No. 13/336,477, filed on Dec. 23, 2011, now Pat. No. 11,690,337.

(30) Foreign Application Priority Data

Dec. 23, 2010 (NL) ..................... 2005919

(51) Int. Cl.
*A01H 6/06* (2018.01)
*A01H 1/00* (2006.01)
*A01H 1/04* (2006.01)
*A01H 5/10* (2018.01)
*A01H 5/12* (2018.01)

(52) U.S. Cl.
CPC ............... *A01H 6/064* (2018.05); *A01H 1/04* (2013.01); *A01H 1/121* (2021.01); *A01H 5/10* (2013.01); *A01H 5/12* (2013.01)

(58) Field of Classification Search
None
See application file for complete search history.

(56) References Cited

U.S. PATENT DOCUMENTS

| | | |
|---|---|---|
| 5,491,295 A | 2/1996 | Niebur et al. |
| 5,506,367 A | 4/1996 | Keaschall |
| 6,812,385 B2 | 11/2004 | Pierce |
| 7,429,694 B2 | 9/2008 | Pierce |
| 2002/0194646 A1 | 12/2002 | Pogue |
| 2004/0078853 A1 | 4/2004 | Pierce |
| 2004/0168231 A1 | 8/2004 | Pierce |
| 2004/0221347 A1 | 11/2004 | Duda et al. |
| 2005/0125863 A1* | 6/2005 | Pierce ............... A01H 5/04 800/300 |
| 2005/0188443 A1 | 8/2005 | Pierce |
| 2006/0085869 A1 | 4/2006 | Pierce |
| 2007/0157333 A1 | 7/2007 | Pierce |
| 2007/0214513 A1 | 9/2007 | Pierce |
| 2010/0235953 A1 | 6/2010 | Trammell |

FOREIGN PATENT DOCUMENTS

WO 91/02787 3/1991

OTHER PUBLICATIONS

Ramin et al, J. of Hortic. Sci. (1994) 69:861-868.*
Pressman et al, J. of Exp. Botany (1987) 38:968-971.*
Roelofse et al, J. of Hort. Science (1989) 64:283-292.*
Staub et al, HortTechnology (1993) 3:291-300.*
Paul et al, J. of Phytological Res. (2005) 18:95-98.*
Welch et al, California Agriculture, Jul. 1978, p. 19.*
Berg et al., Decision on Appeal No. 2022-003691 issued Oct. 14, 2022, in Ex parte Jurgen Berg and Reinier Hendrik Deneer, Appeal No. 2022-003691, U.S. Appl. No. 13/336,477.
*Enzo Biochem, Inc. v. Gen-Probe, Inc.*, 323 F.3d 956 (Fed. Cir. 2002) and submitted with Corrected Appeal Brief filed Jan. 18, 2022 in U.S. Appl. No. 13/336,477.
Ex parte Winner, Appeal 2020-000054 (PTAB 2020), together with therein-Appellant's Sep. 30, 2019 Reply Brief, the therein-Examiner's Jul. 29, 2019 Examiner's Answer, and the therein-Appellant's Apr. 12, 2019 Brief on Appeal, and submitted with Corrected Appeal Brief filed Jan. 18, 2022 in U.S. Appl. No. 13/336,477.
Ex parte Kikuchi, Appeal 2006-03084 (Bd.Pat.App.&Interf. 2007), cited in Reply Brief dated May 25, 2022 in U.S. Appl. No. 13/336,477.
Corrected Appeal Brief dated Jan. 18, 2022 submitted in U.S. Appl. No. 13/336,477.
Reply Brief submitted Dec. 27, 2021 in U.S. Appl. No. 13/336,477.
Declaration of Johan van Huylenbroeck dated May 21, 2021, and submitted with Corrected Appeal Brief filed Jan. 18, 2022 in U.S. Appl. No. 13/336,477.
Bruznican et al., "Celery and Celeriac.: A Critical View on Present and Future,: Breeding," Front Plant Sci. I 0: 1699 (2020) of which Declarant Huylenbroeck is an author and as to which Declarant Huylenbroeck speaks as is qualified to so speak in the Huylenbroeck Declaration.
Declaration of Annemiek Jongenelen-Hermus dated May 20, 2021, and submitted with Corrected Appeal Brief filed Jan. 18, 2022 in U.S. Appl. No. 13/336,477.

(Continued)

*Primary Examiner* — Mykola V. Kovalenko
(74) *Attorney, Agent, or Firm* — Duane Morris LLP; Thomas J. Kowalski

(57) ABSTRACT

The invention relates to a celery plant (*Apium graveolens* L. dulce) carrying a genetic determinant that leads to short leaf blades and/or a more uniform distribution of stem lengths as compared to celery plants not carrying the genetic determinant, wherein said determinant is obtainable by introgression from a plant grown from seed of which a representative sample was deposited with the NCIMB under Accession No. NCIMB 41513. The invention also relates to seeds and other propagation material of the plant and to its progeny as well as to food products that comprise the consumable parts of the plant.

17 Claims, 3 Drawing Sheets
(3 of 3 Drawing Sheet(s) Filed in Color)

(56) References Cited

OTHER PUBLICATIONS

Declaration of inventor Reinier Deneer, dated Jan. 8, 2018, and submitted with Corrected Appeal Brief filed Jan. 18, 2022 in U.S. Appl. No. 13/336,477.
Declaration of Marleen van Luijk dated Nov. 3, 2015, and submitted with Corrected Appeal Brief filed Jan. 18, 2022 in U.S. Appl. No. 13/336,477.
Declaration of Marleen van Luijk, Jun. 24, 2021 (including Appendix 1, slides Marleen van Luijk presented at the Jun. 23, 2021 interview) and submitted with Corrected Appeal Brief filed Jan. 18, 2022 in U.S. Appl. No. 13/336,477.
Declaration of Annemiek Jongenelen-Hermus dated Nov. 1, 2021, and submitted with Corrected Appeal Brief filed Jan. 18, 2022 in U.S. Appl. No. 13/336,477.
Declaration of Marleen van Luijk dated Nov. 2, 2021, and submitted with Corrected Appeal Brief filed Jan. 18, 2022 in U.S. Appl. No. 13/336,477.
Paper Forwarding Appellant's Hearing Demonstrative, and Notice of a Member of the Public Will be Attending the Hearing with presentation accompanying Demonstrative filed Sep. 26, 2022 in US Application No. 13/336/477. Appeal No. 2022-003691.
Transcript of Oral Hearing issued Oct. 25, 2022 in Ex parte Jurgen Berg and Reinier Hendrik Deneer, Appeal No. 2022-003691, U.S. Appl. No. 13/336,477.
D. K. Choudhary, et al., Genetic Divergence in Celery (*Apiurn graveolens*) Journal of Medicinal Aromatic Plant Sciences (2002) vol. 24, p. 683-688.
Natalia Guerra, et al., Quality Characterization of Celery (*Apium graveolens* L.) by Plant Zones and Two Harvest Dates, Journal of Food Science (2010) vol. 75, No. 6, p. S327-S332.
Peter Henderson, Garden and Farm Topics (1884) Peter Henderson & Co., pp. 165-168.
Ramin et al, Manipulation of bolting and flowering in celery (*Apium graveolens* L. var. dulce). III. Effects of photoperiod and irradiance, Jornal of Horticultural Science (1994) 69:861-868.
Weaver, Heirloom Celery Varieties, Apr. 24, 2013, Mother Earth News, accessible at http://www.motherearthnews.com/organic-gardening/heirloom-celery-varieties-zewz1304zsch.aspx#axzz32ZuAPtAR.
*Intervet Inc.*, v. *Merial Limited and Merial SAS*, No. 2009-1568. 617 F.3d 1282 (Fed. Cir. 2010).
*J.E.M. AG Supply* v. *Pioneer Hi-Bred Intern*. Cite as 122 S.Ct. 593 (2001).
Interview with T. Kowalski, et al., Jun. 23, 2021 Interview U.S. Appl. No. 13/336,477, New Celery Morphology, Comments on Cited Documents.
Relevant pages from prosecution of U.S. Appl. No. 14/931,601, including the controlling decision, Ex parte Winner, Appeal 2020-000054, decided Apr. 16, 2020.
Thomas J. Kowalski, et al., Summary of Interview on U.S. Appl. No. 13/336,477 dated Jun. 23, 2021.
Roelofse et al, J. of Hort. Science (1989) 64:283-292; Abstract Only.
E. W. Roelofse, et al., The effect of daylength on the development of glasshouse celery, Journal of Horticultural Science (1989) 64:3, 283-292 (Complete Article).

* cited by examiner

Leaf: length (including petiole) (8)

Leaf: distance between 1st and 2nd pair of leaflets (9)

Leaf: size of the terminal leaflet (10)

Petiole: length (16) width (17)

CELERY MORPHOLOGY

RELATED APPLICATIONS AND INCORPORATION BY REFERENCE

This application is a continuation of U.S. application Ser. No. 13/336,477 filed Dec. 23, 2011, now allowed, which claims benefit of Dutch patent application Serial No. NL2005919 filed 23 Dec. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

Citation or identification of any document in this application is not an admission that such document is available as prior art to the present invention.

It is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U. S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

FIELD OF THE INVENTION

The present invention relates to a new type of celery (*Apium graveolens* L. *dulce*) with a new morphology.

BACKGROUND OF THE INVENTION

*Apium graveolens* is a plant species in the family Apiaceae, and yields two important vegetables known as celery and celeriac. In celery or stalk celery (*Apium graveolens* L. *dulce*), the petiole is the part that is consumed. The petiole carries leaf blades, and a petiole and its leaf blade together form a leaf of the celery plant.

Celery is a vegetable that has a relatively large amount of unusable parts. On average 30% of the plant length is not sold and cut off as waste. In addition, it is economically not very efficient to process celery because the petiole length is very variable as is shown in FIGS. 1 and 2. In order to remove all leaf blades before the celery is sold, sometimes large parts of at least some of the stalks are cut off.

SUMMARY OF THE INVENTION

It is therefore an object of the invention to provide a new type of celery that has a novel morphology so that the processing thereof leads to less waste and making it more suitable for harvesting and packing by machine.

The invention thus relates to a celery plant of the species *Apium graveolens* L. *dulce* carrying a genetic determinant that leads to a shorter leaf blade and/or more uniform petiole lengths within a plant than the existing celery. The advantage hereof is that less waste is produced upon harvest and processing of the plants into sticks or slices, since the leaf blades are shorter. It was found that the shorter leaf blades are the result of shorter internodes.

In one embodiment, the invention thus relates to a celery plant (*Apium graveolens* L. *dulce*) carrying a genetic determinant that leads to short leaf blades and/or a more uniform distribution of stem lengths as compared to a celery plant not carrying the genetic determinant, wherein said determinant is obtainable by introgression from a plant grown from seed of which a representative sample was deposited with the NCIMB under accession number NCIMB 41513.

In one embodiment, said determinant is introgressed from a plant grown from seed that was deposited with the NCIMB under accession number NCIMB 41513.

"Introgression" as used herein is intended to mean introduction of a trait into a plant not carrying the trait by means of crossing and selection in the first generation in which the trait becomes visible. For a dominant trait this is in the F1 of a cross between a plant with the trait and a plant without the trait. For a recessive trait this is suitably the F2.

The invention relates to a celery plant carrying the genetic determinant as present in the genome of seeds deposited as NCIMB 41513, which determinant is obtainable by introgression from a plant grown from seed, a representative sample of which was deposited with the NCIMB under accession number NCIMB 41513.

It should be noted that if the selection criterion or criteria is or are clearly defined, the skilled person will be able to identify the descendants that carry the trait in any further generation. With respect to the determinant of the invention that underlies the development of shorter leaf blades, plants that carry the determinant can suitably be identified among descendants from a cross between a plant not carrying the determinant, and a plant that does carry the said determinant and of which representative seed was deposited under accession numbers NCIMB 41513, by growing F2 plants from seeds that are the result from the initial cross and a selfing step, and selecting plants showing the desired trait.

In one embodiment, the invention relates to a celery plant showing short leaf blades and/or a more uniform distribution of stem lengths as compared to a celery plant not carrying the genetic determinant, which plant is obtainable by:
a) growing plants from seed that was deposited with the NCIMB under accession number NCIMB 41513;
b) crossing the said plant with a plant not showing the trait to obtain an F1 population;
c) selfing plants from the F1 to obtain a F2 population;
d) selecting plants that have short leaf blades and/or a more uniform stem length distribution;
e) optionally repeating steps b) to d).

Plants of the invention were thus also found to show a more uniform distribution of lengths of mature stems within a plant as compared to the lengths of the mature stems of a celery plant not carrying the said genetic determinant. In addition, the new celery type has a significantly shorter length of the complete plant than existing celery types that possess a comparable commercial stick length. The advantage thereof is that less of the usable parts are cut off upon removal of the leaf blades, and the cut-off leaf blades are shorter, thus leading to less waste.

In a further embodiment, the invention relates to celery plants with long sticks and short leaf blades. When celery plants reach a certain length, the separate leaves tend to fall apart. The leaf blades tend to make the plant top-heavy and the plant cannot keep its compact habit. Because of this, only a certain commercial stick-length could until now be developed. Plants with long sticks in this respect are plants of which all sticks are longer than at least 40 cm, preferably longer than at least 45 cm, more preferably longer than at least 50 cm, even more preferably longer than at least 55 cm, most preferably longer than at least 60 cm.

However, since plants of the invention result in stalks with very short leaf blades, in particular due to short internodes, plants with much longer consumable or commercial parts of each stalk are developed using the determinant of the invention. When the critical total plant length of a plant of the invention is reached, and leaves tend to fall apart, the sticks of plants of the invention are much longer than sticks of plants not carrying the genetic determinant of the invention, due to the short leaf blades. Therefore a solution for the impossibility to develop long celery sticks is provided by the present invention.

The leaves of celery are compound leaves that are composed of a petiole, or leaf stem, and a fully subdivided leaf blade. The leaf blade starts at the first joint on the petiole. The leaf blade consists of several pairs of leaflets and ends with a terminal leaflet. A petiole and its leaf blade together form a leaf of the celery plant (FIG. 3).

As used herein the "length of the petiole" and the "stem length" are the distance between the leaf base and the first joint as is indicated in FIG. 3 with the numeral 16. "Stick" and "stalk" also refer to the length of the petiole, as indicated with numeral 16 in FIG. 3; stick is typically used to specify the product after the leaf blades are removed.

The total length is represented in FIG. 3 with reference numeral 8. Total length is also indicated in this description with the terms "total leaf length", "stalk including the leaf blades", or "total plant".

The leaf blade is the part of the leaf excluding the petiole, and this part is indicated in FIG. 3 as (length 8) minus (length 16). The leaf blade is also indicated in this description as "subdivided leaf blade" or "blade". The length of the internodes is the distance between two consecutive pairs of leaflets, for example as indicated with numeral 9 in FIG. 3.

Mature stem length is the stem length (length 16) at the stage of full leaf expansion. Celery plants of the invention show a smaller mature stem length distribution than celery plants that do not carry the genetic determinant of the invention. A smaller mature stem length distribution means that the differences between the lengths of the individual stems are small.

According to the invention the standard deviation of stick lengths in cm within a celery plant is not more than 2.4, preferably not more than 2.2, more preferably not more than 1.8, even more preferably not more than 1.5, most preferably not more than 1.3.

Celery plants of the invention are obtainable by crossing a first celery parent plant with a second celery parent plant, wherein one of the parents is a plant grown from seed of which a representative sample was deposited with the NCIMB under deposit accession number NCIMB 41513 or a progeny plant thereof, and selecting for plants that have one or more of the following features:
  a) shorter leaf blades, in particular due to short internodes, than a celery plant not carrying the said genetic determinant;
  b) a more uniform distribution of stem lengths within a plant as compared to the lengths of the stems of a celery plant not carrying the said genetic determinant;
  c) a shorter total plant length than a celery plant with a comparable petiole length not carrying the said genetic determinant.

In this respect the shorter leaf blades in particular are leaf blades shorter than 30 cm, preferably shorter than 27 cm, more preferably shorter than 24 cm, even more preferably shorter than 21 cm, most preferably shorter than 18 cm.

In this respect the more uniform distribution of stem lengths is in particular expressed as a distribution of which the standard deviation of the stick lengths within a plant is not more than 2.4, preferably not more than 2.2, more preferably not more than 1.8, even more preferably not more than 1.5, most preferably not more than 1.3.

The invention relates to plants in all stages of development even though the characteristics of the new type are not visible in all stages. The plant does however contain in all developmental stages the genetic information that in the ready-to-harvest stage leads to the new celery morphology and thus the new celery type.

The invention furthermore relates to a cell of a celery plant as claimed. Such cell may be either in isolated form or may be part of the complete celery plant or parts thereof and then still constitutes a cell of the invention because such a cell harbours in its genetic constitution the genetic information that leads to the characteristics that define the new celery type. Each cell of celery plants of the invention carries the genetic information that leads to phenotypic expression of said trait. Such a cell of the invention may also be a regenerable cell that can be used to regenerate a new celery plant of the invention.

The invention also relates to tissue of a plant as claimed. The tissue can be undifferentiated tissue or already differentiated tissue. Undifferentiated tissues are for example stem tips, anthers, petals, pollen and can be used in micropropagation to obtain new plantlets that are grown into new plants of the invention. The tissue can also be grown from a cell of the invention.

The invention according to a further aspect thereof relates to seeds of plant as claimed. Although the seeds do not show the characteristics of the celery of the invention they harbour the genetic information that when a plant is grown from the seeds makes this plant a plant of the invention.

The invention also relates to progeny of the plants, cells, tissues and seeds of the invention. Such progeny can in itself be plants, cells, tissues or seeds.

As used herein the word "progeny" is intended to mean the first and all further descendants from a cross with a plant of the invention that shows short leaf blades and/or a more uniform distribution of stem lengths as compared to a celery plant not carrying the genetic determinant of the invention. Progeny of the invention are descendants of any cross with a plant of the invention that carries the determinant that leads to shorter leaf blades due to short internodes and/or a more uniform distribution of stem lengths. In one embodiment, the progeny plant has the novel and inventive combination of morphological and physiological characteristics of the claimed plant, representative seed of which was deposited under NCIMB Accession No. 41513. Such progeny has the same characteristics as claimed for the plant of the invention and may be modified in one or more other characteristics. Such additional modifications are for example effected by mutagenesis or by transformation with a transgene.

"Progeny" also encompasses plants that carry the determinant of the invention and are obtained from other plants or progeny of plants of the invention by vegetative propagation or multiplication.

The term 'genetic determinant' as used herein encompasses one or more genes or alleles. These terms are used interchangeably.

The 'genetic trait' is the trait or characteristic that is conferred by the genetic determinant. The genetic trait can be identified phenotypically. However, also plant stages for which no phenotypic observance can be performed do carry the genetic information that leads to the genetic trait. 'Trait' or 'phenotypic trait' can be used instead of 'genetic trait'.

The trait of the invention as used herein is referred to as short leaf blades and/or a more uniform distribution of stem lengths. The mention of this trait is always intended to be compared to a reference. Therefore, as used herein, these are short leaf blades and/or a more uniform distribution of stem lengths as compared to celery plants not carrying the genetic determinant of the invention. In a preferred aspect the trait of the invention comprises short leaf blades and a more uniform distribution of stem lengths.

In the absence of molecular markers, equivalence of genetic determinants can be determined by an allelism test. To perform an allelism test, material that is homozygous for the known determinant is crossed with material that is homozygous for the phenotypic trait to be tested. When no segregation for the trait to be observed is present in the F2 of the cross, the genetic determinants resulting in the phenotypic trait have been proven to be the same.

When more than one gene is responsible for a certain trait, and an allelism test is done to determine equivalence, the skilled person doing the test has to ascertain that all relevant genes are present homozygously in order for the test to work properly.

The invention thus further relates to seed of the claimed plant and to parts of the plant that are suitable for sexual reproduction. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, protoplasts.

According to a further aspect thereof the invention provides a tissue culture of a plant carrying the genetic determinant of the invention. The tissue culture comprises regenerable cells. Such tissue culture can be derived from leaves, pollen, embryos, cotyledon, hypocotyls, meristematic cells, roots, root tips, anthers, flowers, seeds and stems. The tissue culture can be regenerated into a plant carrying the genetic determinant of the invention. Suitably a regenerated plant expresses the phenotype of short leaf blades and/or a more uniform distribution of stem lengths as compared to celery plants not carrying the genetic determinant.

According to another aspect of the invention plants are provided that have all of the morphological and physiological characteristics of plants of the invention, representative seed of which was deposited under NCIMB Accession No. 41513 which plants are grown from seeds of the plant of the invention or regenerated from parts thereof, or from a tissue culture.

According to a further aspect of the invention the sticks are solid.

The invention furthermore relates to hybrid seed and to a method of producing hybrid seed comprising crossing a first parent plant with a second parent plant and harvesting the resultant hybrid seed, wherein said first parent plant and/or said second parent plant is the plant as claimed. Suitably a hybrid plant expresses the phenotype of short leaf blades and/or a more uniform distribution of stem lengths as compared to celery plants not carrying the genetic determinant.

The invention also relates to inbreds and doubled haploids.

In one embodiment, the invention relates to a celery plant comprising the trait of the invention, which plant is obtainable by:
 a) crossing a plant, representative seed of which was deposited with the NCIMB under accession number NCIMB 41513, with a plant not showing the trait to obtain an F1 population;
 b) selfing plants from the F1 population to obtain an F2 population;
 c) selecting in said F2 for plants that have the trait of the invention; and
 d) optionally performing one or more additional rounds of selfing or crossing, and subsequently selecting, for the trait.

In one embodiment, the invention relates to celery plants that carry the determinant of the invention and having acquired said determinant by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the genetic information is acquired is formed by plants grown from seeds of which a representative sample was deposited under accession number NCIMB 41513 or from the deposited seeds or sexual or vegetative descendants thereof.

The invention also relates to the germplasm of plants of the invention. The germplasm is constituted by all inherited characteristics of an organism and according to the invention encompasses at least the trait of the invention.

The invention also relates to the celery stems or sticks that are produced by the plants of the invention. In addition, the invention relates to parts of the leaves and processed products produced from the leaves, and to the whole marketable celery plant without the roots. A marketable celery plant that carries the trait of the invention has a much higher uniformity of stick lengths, resulting in a more uniform product and less waste. In addition, a celery plant that carries the phenotypic trait of the invention has much shorter leaf blades, which are typically the parts of the plant that are discarded. Therefore the use of celery plants of the invention results in a significantly lower quantity of waste material.

The trait of the invention is recognizable in a celery plant when the leaf blades are significantly shorter due to short internodes. Significantly shorter or short leaf blades means at least 20% shorter, preferably at least 30% shorter, more preferably at least 40% shorter, even more preferably at least 45% shorter, most preferably at least 50% shorter when compared to a celery plant not carrying the genetic determinant of the invention. Short internodes refers to at least the first internode being at least 30% shorter, preferably at least 40% shorter, more preferably at least 50% shorter, even more preferably at least 60% shorter, most preferably at least 70% shorter than the first internode of a celery plant not carrying the genetic determinant.

The short leaf blades of the invention result in leaf blades that are shorter than 30 cm, preferably shorter than 27 cm, more preferably shorter than 24 cm, even more preferably shorter than 21 cm, most preferably shorter than 18 cm.

In one aspect the invention relates to a method for production of a celery plant comprising short leaf blades and/or a more uniform distribution of stem lengths, comprising
- a) crossing a plant comprising the genetic determinant that leads to expression of short leaf blades and/or a more uniform distribution of stem lengths with another plant;
- b) selfing the resulting F1 for obtaining F2 plants;
- c) selecting plants comprising short leaf blades and/or a more uniform distribution of stem lengths in the F2;
- d) optionally performing one or more additional rounds of selfing or crossing, and subsequently selecting, for a plant comprising short leaf blades and/or a more uniform distribution of stem lengths.

It is clear that the parent that provides the trait of the invention is not necessarily a plant grown directly from the deposited seeds. The parent can also be a progeny plant from the seed or a progeny plant from seeds that are identified to have the trait of the invention by other means.

In one aspect, the invention relates to a method for production of a celery plant comprising short leaf blades and/or a more uniform distribution of stem lengths, comprising:
- a) crossing a plant comprising the genetic determinant that leads to expression of short leaf blades and/or a more uniform distribution of stem lengths with another plant;
- b) optionally backcrossing the resulting F1 with the preferred parent;
- c) selecting for plants comprising short leaf blades and/or a more uniform distribution of stem lengths in the F2;
- d) optionally performing one or more additional rounds of selfing or crossing, and subsequently selecting, for a plant comprising short leaf blades and/or a more uniform distribution of stem lengths.

The invention additionally provides a method of introducing a desired trait into a celery plant comprising short leaf blades and/or a more uniform distribution of stem lengths, comprising:
- a) crossing a celery plant comprising short leaf blades and/or a more uniform distribution of stem lengths, representative seed of which were deposited with the NCIMB under deposit number NCIMB 41513, with a second celery plant that comprises a desired trait to produce F1 progeny;
- b) selecting an F1 progeny that comprises short leaf blades and/or a more uniform distribution of stem lengths and the desired trait;
- c) crossing the selected F1 progeny with either parent, to produce backcross progeny;
- d) selecting backcross progeny comprising the desired trait and short leaf blades and/or a more uniform distribution of stem lengths; and
- e) optionally repeating steps (c) and (d) one or more times in succession to produce selected fourth or higher backcross progeny that comprises the desired trait and short leaf blades and/or a more uniform distribution of stem lengths. The invention includes a celery plant produced by this method.

In one embodiment selection for plants comprising short leaf blades and/or a more uniform distribution of stem lengths is done in the F1. In another aspect, selection for the trait of the invention is started in the F2 of a cross or alternatively of a backcross.

In one embodiment selection for plants comprising short leaf blades and/or a more uniform distribution of stem lengths is started in the F3 or a later generation.

In one embodiment the plant comprising the genetic determinant is a plant of an inbred line, a hybrid, a doubled haploid, or of a segregating population.

The invention further provides a method for the production of a celery plant comprising short leaf blades and/or a more uniform distribution of stem lengths by using a doubled haploid generation technique to generate a doubled haploid line comprising the said short leaf blades and/or a more uniform distribution of stem lengths.

The invention furthermore relates to hybrid seed and to a method for producing hybrid seed comprising crossing a first parent plant with a second parent plant and harvesting the resultant hybrid seed, wherein said first parent plant and/or said second parent plant is the plant as claimed.

In one embodiment, the invention relates to a method for producing a hybrid celery plant comprising crossing a first parent celery plant with a second parent celery plant and harvesting the resultant hybrid celery seed, in which the first parent celery plant and/or the second parent celery plant comprises short leaf blades and/or a more uniform distribution of stem lengths.

The invention also relates to a method for the production of a celery plant comprising short leaf blades and/or a more uniform distribution of stem lengths by using a seed that comprises a genetic determinant in its genome that leads to short leaf blades and/or a more uniform distribution of stem lengths for growing the said celery plant. The seeds are suitably seeds of which a representative sample was deposited with the NCIMB under deposit number NCIMB 41513.

The invention also relates to a method for seed production comprising growing celery plants from seeds of which a representative sample was deposited with the NCIMB under deposit number NCIMB 41513, allowing the plants to produce seeds, and harvesting those seeds. Production of the seeds is suitably done by crossing or selfing.

In one embodiment, the invention relates to a method for the production of a celery plant comprising short leaf blades and/or a more uniform distribution of stem lengths by using tissue culture. The invention furthermore relates to a method for the production of a celery plant comprising short leaf blades and/or a more uniform distribution of stem lengths by using vegetative reproduction.

In another embodiment, the invention relates to a method for the production of a celery plant comprising short leaf blades and/or a more uniform distribution of stem lengths by using a method for genetic modification to introgress short leaf blades and/or a more uniform distribution of stem lengths into the celery plant. Genetic modification comprises transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of celery plants that comprise short leaf blades and/or a more uniform distribution of stem lengths wherein germplasm comprising short leaf blades and/or a more uniform distribution of stem lengths is used. Representative seed of said plant comprising the genetic determinant and being representative for the germplasm was deposited with the NCIMB under deposit number NCIMB 41513.

In a further embodiment the invention relates to a method for the production of a celery plant comprising short leaf blades and/or a more uniform distribution of stem lengths wherein progeny or propagation material of a plant comprising the genetic determinant conferring said short leaf blades and/or a more uniform distribution of stem lengths is used as a source to introgress short leaf blades and/or a more uniform distribution of stem lengths into another celery plant. Representative seed of said plant comprising the genetic determinant was deposited with the NCIMB under deposit number NCIMB 41513.

The invention provides preferably a celery plant showing short leaf blades and a more uniform distribution of stem lengths, which plant is obtainable by any of the methods herein described.

Deposit

Seeds of *Apium graveolens* 07.8733 that comprise the genetic determinant of the invention which leads to short leaf blades and/or a more uniform distribution of stem lengths were deposited with NCIMB Ltd, Ferguson Building, Craibstone 5 Estate, Bucksburn, Aberdeen AB21 9YA Scotland, UK on 22 Oct. 2007 under deposit accession number NCIMB 41513. The Deposit with the NCIMB, under deposit accession number NCIMB 41513 was made and accepted pursuant to the terms of the Budapest Treaty. The deposit will be irrevocably and without restriction or condition released to the public upon the issuance of a patent and for the enforceable life of the patent. Upon issuance of a patent, all restrictions upon the deposit will be removed, and the deposit is intended to meet the requirements of 37 CFR §§ 1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will be further illustrated in the Examples that follow. In the Example reference is made to the following figures.

EXAMPLES

Example 1

Creation of Celery Plants of the Invention

In research that led to the invention, a cross was made between 2 fertile plants from lines from *Apium graveolens dulce* (celery or stalk celery) and *Apium graveolens secalinum* (cutting celery or leaf celery). The crosses have been made with insects. In the F2 of this specific cross, plants with an unexpected different habit were found.

*A. graveolens secalinum* is known for its use of the leaves, and the plants therefore mainly consist of long leaf blades and thin petioles, as opposite to *A. graveolens dulce*, which is specifically used for the thick petioles or sticks. *A. graveolens dulce* contains on the end of the petioles also long leaf blades with long internodes. However, in the progeny of the cross between *dulce* and *secalinum*, surprisingly some plants with a different morphology were identified.

These plants had unexpectedly resulted in shorter leaf blades with short internodes in combination with the long and thick petioles from *dulce*. This was in contradiction to the expected longer and pronounced leaf blades that are typical for leaf celery, and that are also standard in the stalk celery. Therefore, the two parents with long leaf blades and long internodes produced progeny plants with short leaf blades and short internodes.

Figure 4:
FIG. 4 shows on the left two normal celery plants and on the right two plants of the invention.

Further development was carried out through inbred and half-sib selection. After several cycles the new type became more uniform with the first joints on the same height (FIG. 4), resulting in a distribution of petiole lengths within a plant with a low standard deviation. The differences in length of the individual petioles of a plant were very small. This results in a very uniform harvestable product, as there is a high number of sticks almost the same length. It also results in a lower amount of waste, as less cutting of the sticks needs to be done to acquire sticks of the same length.

Also the leaf tips are uniform on the same height. Furthermore, the leaf blades above the joint are significantly shorter in the new type in comparison with a normal celery plant. Since the leaf blades of celery are typically not used and need to be cut off and disposed of, the much shorter leaf blades result in a considerably lower amount of waste.

Example 2

Characterisation of Celery Plants of the Invention

Figure 5A:
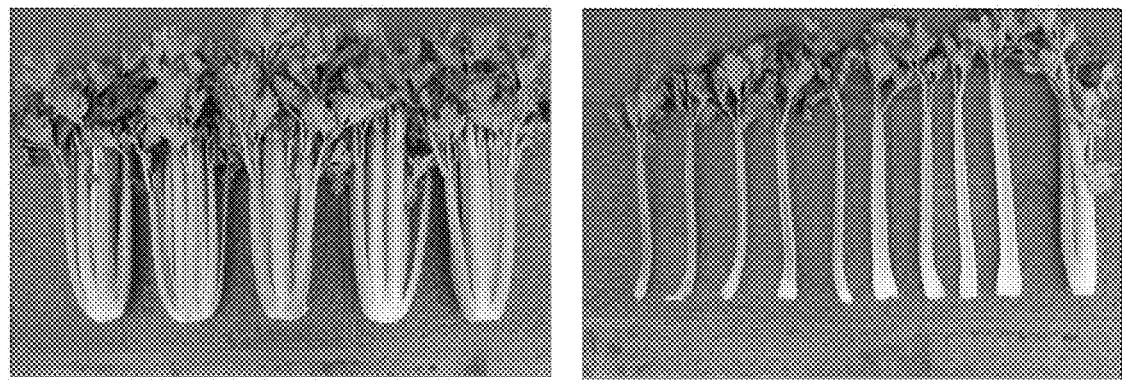
FIG. 5A shows plants of the invention with separated leaves.
Figure 5B:
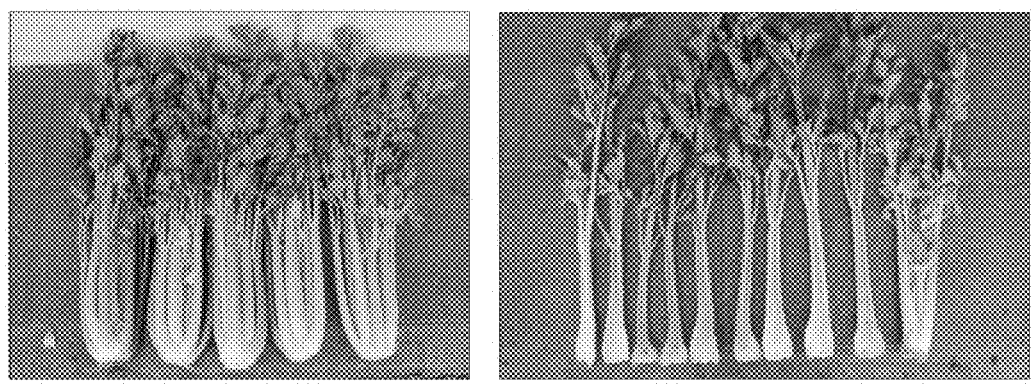
FIG. 5B shows a normal celery plant.

Plants of the invention (identified herein as "newcel") were compared with known celery plants. Table 1 shows the results of this comparison. FIG. 5A shows plants of the invention with separated leaves. FIG. 5B shows a normal celery plant.

TABLE 1

Figure 1:
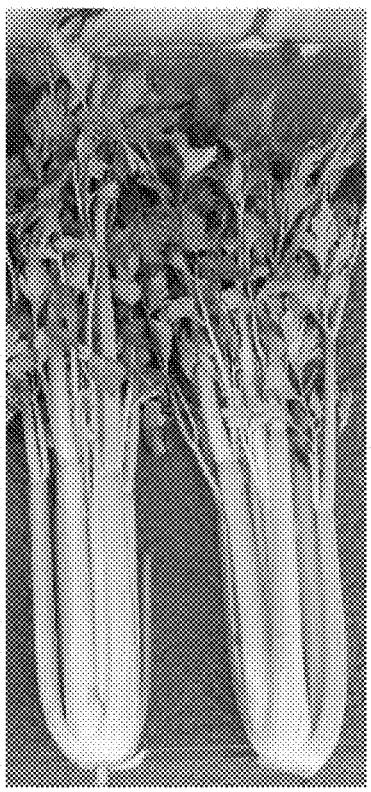
FIG. 1 shows the entire celery plant of the existing type.
Figure 2:
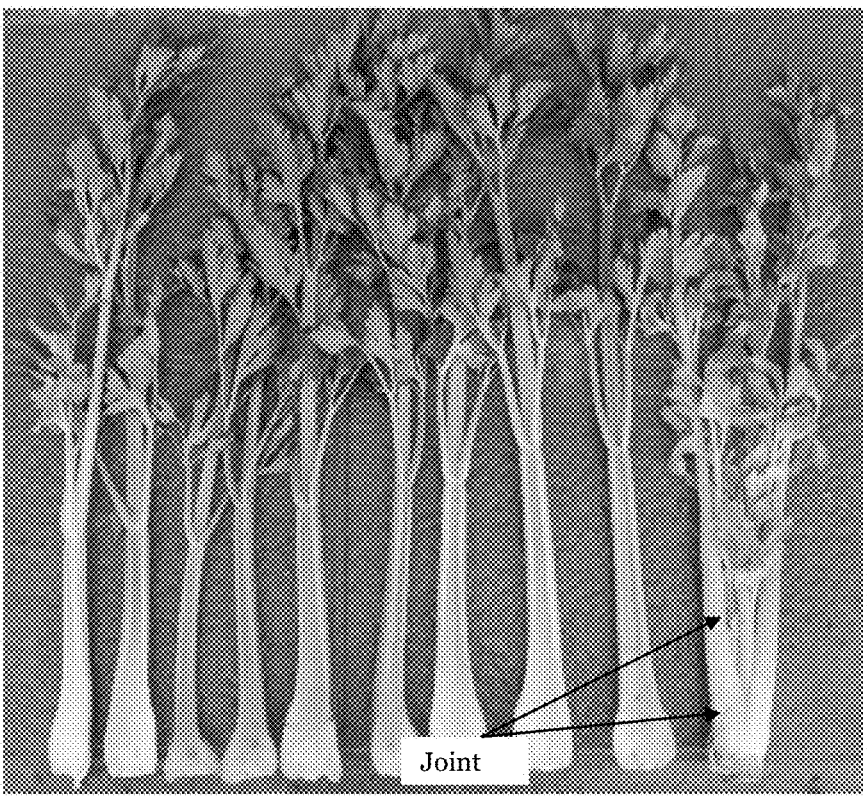
FIG. 2 shows the different stems and heart of the celery plant of FIG. 1.
Figure 3:
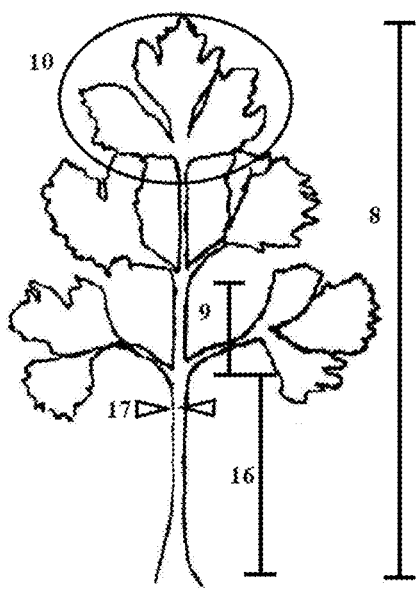
FIG. 3 illustrates the description of a celery leaf according to UPOV TG/82/4.

| | # sticks per plant | total length (cm): (8) as in Fig 3 | average leaf blade length (cm) | average stick length (cm) | st. dev. sticks |
|---|---|---|---|---|---|
| "newcel" | | | | | |
| Plant 1 | 13 | 39 | 17.9 | 21.1 | 1.0 |
| Plant 2 | 11 | 39 | 17.1 | 21.9 | 1.1 |
| Plant 3 | 12 | 43 | 20.7 | 22.3 | 1.1 |
| Plant 4 | 12 | 40 | 16.4 | 23.6 | 1.5 |
| Plant 5 | 10 | 40 | 17.3 | 22.7 | 1.2 |
| Plant 6 | 13 | 41 | 18.8 | 22.2 | 1.6 |

TABLE 1-continued

| | # sticks per plant | total length (cm): (8) as in Fig 3 | average leaf blade length (cm) | average stick length (cm) | st. dev. sticks |
|---|---|---|---|---|---|
| Plant 7 | 12 | 41 | 18.1 | 22.9 | 1.3 |
| Plant 8 | 14 | 41 | 19.4 | 21.6 | 1.2 |
| Plant 9 | 11 | 41 | 19.2 | 21.8 | 1.8 |
| Plant 10 | 12 | 40 | 18.3 | 21.7 | 1.5 |
| Average Normal celery | 12.0 | 40.5 | 18.3 | 22.2 | 1.3 |
| Plant 1 | 13 | 59 | 36.7 | 22.3 | 3.2 |
| Plant 2 | 11 | 66 | 38.1 | 27.9 | 3.4 |
| Plant 3 | 12 | 61 | 37.2 | 23.8 | 2.5 |
| Plant 4 | 12 | 60 | 34.9 | 25.1 | 4.6 |
| Plant 5 | 11 | 58 | 32.6 | 25.4 | 4.5 |
| Plant 6 | 12 | 58 | 32.6 | 25.4 | 4.6 |
| Plant 7 | 12 | 68 | 42.2 | 25.8 | 4.5 |
| Plant 8 | 13 | 62 | 38.3 | 23.7 | 2.8 |
| Plant 9 | 11 | 59 | 34.0 | 25.0 | 3.2 |
| Plant 10 | 12 | 60 | 36.2 | 23.8 | 4.1 |
| Average | 11.9 | 61.1 | 36.3 | 24.8 | 3.7 |

It is clear from the results in Table 1 that the celery plants of the invention have significantly shorter leaf blades, a significantly shorter total length than celery plants with a comparable stick length not carrying the genetic determinant of the invention, and in addition stem length distribution within a plant is significantly more uniform in comparison with normal celery.

Example 3

Introduction of the New Trait into Other Celery Plants

Plants of the invention that were deposited under NCIMB accession number 41513 were crossed with normal celery plants. The F2 progeny segregated for plants that showed the same characteristics as the parent plants of NCIMB accession number 41513. Further development of these plants resulted in lines with the trait of the invention, as found in NCIMB accession number 41513.

The invention claimed is:

1. A celery plant (*Apium graveolens* L. *dulce*) having a ratio between average leaf blade length in cm and average stick length in cm of less than 1.0 and a standard deviation of stick lengths in cm within the plant of not more than 2.4 at the stage of full leaf expansion, wherein the celery plant comprises a genetic determinant that confers the ratio between average leaf blade length in cm and average stick length in cm of less than 1.0 and a standard deviation of stick lengths in cm within the plant of not more than 2.4 at the stage of full leaf expansion, and wherein a representative deposit of seed comprising the genetic determinant has been deposited with the NCIMB under Accession No. 41513.

2. The celery plant as claimed in claim 1, wherein the celery plant has leaf blades shorter than 27 cm.

3. The celery plant as claimed in claim 1, wherein the celery plant has leaf blades shorter than 18 cm.

4. The celery plant as claimed in claim 1, wherein the standard deviation of stick length in cm within the celery plant is not more than 1.8.

5. The celery plant as claimed in claim 1, wherein the standard deviation of stick length in cm within the celery plant is not more than 1.3.

6. Seed of the celery plant as claimed in claim 1, said seed having the genetic determinant that confers the ratio between average leaf blade length in cm and average stick length in cm of less than 1.0 and the standard deviation of stick lengths in cm within the plant of not more than 2.4 at the stage of full leaf expansion, and a plant grown from said seed has the ratio between average leaf blade length in cm and average stick length in cm of less than 1.0 and the standard deviation of stick lengths in cm within the plant of not more than 2.4 at the stage of full leaf expansion, and wherein a representative deposit of seed comprising the genetic determinant has been deposited with the NCIMB under Accession No. 41513.

7. Propagation material of the celery plant of claim 1, said propagation material having the genetic determinant that confers the ratio between average leaf blade length in cm and average stick length in cm of less than 1.0 and the standard deviation of stick lengths in cm within the plant of not more than 2.4 at the stage of full leaf expansion; and wherein a representative deposit of seed comprising the genetic determinant has been deposited with the NCIMB under Accession No. 41513, and said propagation material comprises microspores, pollen, ovaries, ovules, embryo sacs, egg cells, cuttings, roots, stems, cells, protoplasts, leaves, cotyledon, hypocotyls, meristematic cells, root tips, anthers, flowers, or seeds, and a plant from said propagation material has the ratio between average leaf blade length in cm and average stick length in cm of less than 1.0 and the standard deviation of stick lengths in cm within the plant of not more than 2.4 at the stage of full leaf expansion.

8. The celery plant as claimed in claim 1, wherein the celery plant has been grown from seed which has been deposited with the NCIMB under Accession No. 41513.

9. A food product comprising stalks of the celery plant as claimed in claim 1.

10. A celery plant (*Apium graveolens* L. *dulce*) having a genetic determinant,
wherein in a plant grown from seed deposited with the NCIMB under Accession No. 41513, said genetic determinant confers a ratio between average leaf blade length in cm and average stick length in cm of less than 1.0 and a standard deviation of stick lengths in cm within that plant of not more than 2.4 at the stage of full leaf expansion, and
wherein a representative deposit of seed comprising the genetic determinant has been deposited with the NCIMB under Accession No. 41513.

11. A method of introducing a genetic determinant into a celery plant not exhibiting a ratio between average leaf blade length in cm and average stick length in cm of less than 1.0 and a standard deviation of stick lengths in cm within the celery plant of not more than 2.4 at the stage of full leaf expansion, said method comprising crossing the celery plant with the celery plant of claim 1, wherein said genetic determinant confers the ratio between average leaf blade length in cm and average stick length in cm of less than 1.0 and the standard deviation of stick lengths in cm within the celery plant of claim 1 of not more than 2.4 at the stage of full leaf expansion, and wherein a representative deposit of seed comprising the genetic determinant has been deposited with the NCIMB under Accession No. 41513.

12. The celery plant as claimed in claim 1, wherein the celery plant has leaf blades shorter than 21 cm.

13. The celery plant as claimed in claim 1, wherein the standard deviation of stick length in cm within the celery plant is not more than 2.2.

14. The celery plant as claimed in claim 1, wherein the standard deviation of stick length in cm within the celery plant is not more than 1.5.

15. Seed of the celery plant as claimed in claim 10, said seed having the genetic determinant of the celery plant grown from seed deposited with the NCIMB under Accession No. 41513 that confers the ratio between average leaf blade length in cm and average stick length in cm of less than 1.0 and the standard deviation of stick lengths in cm within that plant of not more than 2.4 at the stage of full leaf expansion, and wherein a representative deposit of seed comprising the genetic determinant has been deposited with the NCIMB under Accession No. 41513.

16. Propagation material of a celery plant (*Apium graveolens* L. *dulce*), said propagation material having a genetic determinant of a celery plant grown from seed deposited with the NCIMB under Accession No. 41513 that confers a ratio between average leaf blade length in cm and average stick length in cm of less than 1.0 and a standard deviation of stick lengths in cm within that plant of not more than 2.4 at the stage of full leaf expansion; and wherein a representative deposit of seed comprising the genetic determinant has been deposited with the NCIMB under Accession No. 41513, and said propagation material comprises microspores, pollen, ovaries, ovules, embryo sacs, egg cells, cuttings, roots, stems, cells, protoplasts, leaves, cotyledon, hypocotyls, meristematic cells, root tips, anthers, flowers, or seeds.

17. Seed which has been deposited with the NCIMB under Accession No. 41513.

* * * * *